(12) United States Patent
Hwang et al.

(10) Patent No.: US 10,289,803 B2
(45) Date of Patent: May 14, 2019

(54) METHOD OF DETERMINING PATIENT CASE IDENTITY IN DIGITAL PATHOLOGY SYSTEM

(71) Applicant: Infinitt Healthcare Co., Ltd., Seoul (KR)

(72) Inventors: Man Won Hwang, Incheon (KR); Sung Yong Kim, Seoul (KR); Duy Hien Pham, Seoul (KR); Myung Jin Kim, Gyeonggi-do (KR)

(73) Assignee: INFINITT HEALTHCARE CO., LTD., Seoul (KR)

( * ) Notice: Subject to any disclaimer, the term of this patent is extended or adjusted under 35 U.S.C. 154(b) by 350 days.

(21) Appl. No.: 15/217,356

(22) Filed: Jul. 22, 2016

(65) Prior Publication Data
US 2018/0018426 A1    Jan. 18, 2018

(30) Foreign Application Priority Data

Jul. 12, 2016  (KR) .......................... 10-2016-0087789

(51) Int. Cl.
*G06K 9/00*     (2006.01)
*G06F 19/00*    (2018.01)
(Continued)

(52) U.S. Cl.
CPC ............ *G06F 19/321* (2013.01); *G06F 19/00* (2013.01); *G06K 9/6203* (2013.01);
(Continued)

(58) Field of Classification Search
None
See application file for complete search history.

(56) References Cited

U.S. PATENT DOCUMENTS 8,244,021 B2 *   8/2012   Lett ..................... G01N 21/6428
                                                       382/128
9,984,457 B2 *   5/2018   Hall ...................... G06T 11/203
(Continued)

FOREIGN PATENT DOCUMENTS

KR         10-1559798         10/2015

OTHER PUBLICATIONS

English translation of 10-1559798.

*Primary Examiner* — Shervin K Nakhjavan
(74) *Attorney, Agent, or Firm* — Novick, Kim & Lee, PLLC; Sang Ho Lee (57) ABSTRACT

Disclosed is a patient case identity determination method for a digital pathology system, which is performed by a patient case identity determination unit. The patient case identity determination method includes acquiring a digital slide image from a scanner; requesting a laboratory information system (LIS) to send patient/case information including a preprocessing step image that is obtained in a digital slide preprocessing step associated with the digital slide image; receiving the patient/case information including the preprocessing step image from the LIS; comparatively analyzing a pattern of the digital slide image and the preprocessing step image to calculate a synchronization rate and stores the calculated synchronization rate; and providing information about whether the digital slide image is identical to the patient/case information based on the calculated synchronization rate when a client application provides a reading of the digital slide image.

9 Claims, 8 Drawing Sheets

(51) Int. Cl.
  *G06T 7/00*      (2017.01)
  *G06T 7/60*      (2017.01)
  *G06K 9/62*      (2006.01)
  *G06T 7/30*      (2017.01)
  *G06T 7/13*      (2017.01)

(52) U.S. Cl.
  CPC .............. *G06T 7/0012* (2013.01); *G06T 7/13* (2017.01); *G06T 7/30* (2017.01); *G06T 7/60* (2013.01); *G06T 2207/20112* (2013.01); *G06T 2207/30004* (2013.01)

(56) References Cited

U.S. PATENT DOCUMENTS

| | | | | |
|---|---|---|---|---|
| 2003/0012420 A1* | 1/2003 | Verwoerd | ............ | G06T 7/0012 382/133 |
| 2004/0170325 A1* | 9/2004 | Eichhorn | ........... | G06K 9/00147 382/205 |
| 2009/0214088 A1* | 8/2009 | Sorenson | ............... | G01N 1/312 382/128 |
| 2011/0060766 A1* | 3/2011 | Ehlke | .................... | G06F 3/0481 707/802 |
| 2012/0069049 A1* | 3/2012 | Howe | ................ | G06K 9/00134 345/629 |
| 2012/0072452 A1* | 3/2012 | Stratman | ............ | G06F 19/366 707/772 |
| 2012/0257811 A1* | 10/2012 | Metzger | ................ | G06T 7/0012 382/133 |
| 2012/0275671 A1* | 11/2012 | Eichhorn | ............. | G06T 7/0004 382/128 |
| 2013/0194312 A1* | 8/2013 | Yoshioka | ............ | G02B 21/365 345/672 |
| 2014/0278540 A1* | 9/2014 | Kyusojin | ............ | G06F 19/321 705/3 |
| 2015/0293941 A1* | 10/2015 | Eichhorn | ............ | G06F 19/321 707/723 |
| 2017/0103521 A1* | 4/2017 | Chukka | ................ | G06K 9/0014 |

* cited by examiner

| Number of objects | Object size | arrangement | Type |
|---|---|---|---|
| Single Object | Object size/ROI size < 0.6 | - | Type 1 |
|  | Object size/ROI size >= 0.6 | - | Type 2 |
| Multi objects | Object size/ROI size < 0.6 | Row | Type 3 |
|  |  | Col | Type 4 |
|  |  | Mix | Type 5 |
|  | Object size/ROI size >=0.6 | Row | Type 6 |
|  |  | Col | Type 7 |
|  |  | Mix | Type 8 |

METHOD OF DETERMINING PATIENT CASE IDENTITY IN DIGITAL PATHOLOGY SYSTEM

CROSS-REFERENCE TO RELATED APPLICATION

This application claims priority to and the benefit of Korean Patent Application No. 2016-0087789, filed on Jul. 12, 2016, the disclosure of which is incorporated herein by reference in its entirety.

BACKGROUND

1. Field

The present invention relates to a method of determining patient case identity in a digital pathology system, and more particularly, to a patient case identity determination method for a digital pathology system that may solve a problem in which human errors are likely to occur when a task of adding a manual barcode is performed in each of the preprocessing steps of producing a digital slide image, i.e., grossing, waxing, paraffin blocking, sectioning, or staining.

2. Discussion of Related Art

Pathology is a basic medical science for studying a state of a disease or a change in a tissue structure, an organic form, or an organic function of a pathogen in order to find a cause of the disease.

In particular, digital pathology is an image-based information environment which is enabled by computer technology that allows for the management of information generated from a digital slide. Digital pathology is enabled in part by virtual microscopy, which is the practice of producing an image with a microscope and delivering the produced image to a computer network.

Digital pathology is globally recognized as an emerging field of diagnostic medicine. This is because, compared to a well-known and existing method, digital pathology may achieve even better, faster and cheaper diagnosis, prognosis and prediction of cancer which is the biggest enemy of modern people's health or other important diseases.

As in the above, digital pathology is getting the spotlight as an emerging field of diagnostic medicine. However, the research and development is still in an early stage. The current stage of the research and development can be guessed from the following circumstance. In Korea, there is little research and development on a digital pathology system, and also there is no product associated with the research and development. Even in foreign countries, there is no digital pathology system that is approved for primary diagnosis by the U.S. Food and Drug Administration (FDA).

In such a digital pathology system, a task of adding a manual barcode is performed in each of the preprocessing steps of producing a digital slide image, i.e., grossing, waxing, paraffin blocking, sectioning, or staining. However, human errors are likely to occur in this system, and actually multiple errors do have occurred.

Examining related patent documents, Korean Patent No. 10-1559798, which was registered on Oct. 6, 2015, discloses a method for normalizing an image in digital pathology. In detail, the above patent document discloses the steps of choosing a sample for image normalization, analyzing a spectrum of a certain part of the chosen sample to collect information about a material included in the certain part of the sample, finding a correlation equation through the collected information, correcting the entire image of the sample using the correlation equation, and normalizing an image of the sample through the corrected image.

However, the related patent document says nothing about a technology for recognizing and preventing a problem of the human errors as described above.

SUMMARY

The present invention provides a patient case identity determination method for a digital pathology system that may solve a problem in which human errors are likely to occur when a task of adding a manual barcode is performed in each of the preprocessing steps of producing a digital slide image, i.e., grossing, waxing, paraffin blocking, sectioning, or staining.

According to an aspect of the present disclosure, there is provided a patient case identity determination method for a digital pathology system, which is performed by a patient case identity determination unit. The patient case identity determination method includes acquiring a digital slide image from a scanner; requesting a laboratory information system (LIS) to send patient/case information including a preprocessing step image that is obtained in a digital slide preprocessing step associated with the digital slide image; receiving the patient/case information including the preprocessing step image from the LIS; comparatively analyzing a pattern of the digital slide image and the preprocessing step image to calculate a synchronization rate and storing the calculated synchronization rate; and providing information about whether the digital slide image is identical to the patient/case information based on the calculated synchronization rate when a client application provides a reading of the digital slide image.

The client application may be a terminal configured to inquire about the digital slide image, analyze the digital sidle image, write an expert opinion on the digital slide image, or download the digital slide image.

The patient case identity determination method may further include updating the patient/case information when the synchronization rate satisfies a certain criterion.

When the digital slide image is regarded as a first digital slide image, and the preprocessing step image is regarded as a second digital slide image, the comparatively analyzing of a pattern of the first digital slide image and the second digital slide image to calculate a synchronization rate may include extracting a first main area and a second main area of each of the first digital slide image and the second digital slide image; aligning the first main area and the second main area; classifying sample types of the first main area and the second main area when the alignment is successful; and measuring similarity of the first main area and the second main area when the sample types are the same.

The classifying of sample types may include determining whether there is a single sample or there are multiple samples through the number of central points detected in the first main area and the second main area; determining sizes of the samples of the first main area and the second main area; determining an arrangement shape of the samples as one of a vertical arrangement, a horizontal arrangement, and a mixture arrangement through an up-down and left-right position relation between the detected central points, and classifying types of the samples on the basis of the singularity/plurality determination for the samples, the sizes of the samples, and the arrangement shape of the samples.

The measuring of similarity of the first main area and the second main area may include, when there is a single sample, measuring the similarity through shape information of the sample, color information of the sample, and edge directivity and intensity of the sample, wherein the edge directivity and intensity of the sample are measured by performing cutting with three concentric circles and at an angle of 45 degrees with respect to edge points corresponding to the first main area and the second main area, performing a division into 24 sections to set a search section, each section including the number of surrounding edge points in the section, average color information of the surrounding edge points in the section, average edge intensity of the surrounding edge points in the section, and vector direction information of the surrounding edge points in the section, and comparing information about the 24 sections of the edge points corresponding to the first main area and the second main area.

The measuring of similarity of the first main area and the second main area may include, when there are multiple samples, measuring the similarity through shape information of the sample, color information of the sample, and edge directivity and intensity of the sample, information regarding distances between objects in the sample, and a cluster shape in which the objects are formed.

The patient case identity determination method may further include determining that the sample similarity measurement has failed when the alignment fails.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Hereinafter, preferred embodiments of the present invention will be described below in more detail with reference to the accompanying drawings. Terms and words used in the specification and the claims shall not be interpreted as commonly-used dictionary meanings, but shall be interpreted as to be relevant to the technical scope of the invention based on the fact that the inventor may properly define the concept of the terms to explain the invention in best ways.

Therefore, the embodiments and the configurations depicted in the drawings are for illustrative purposes only and are not intended to represent all technical scope of the embodiments, so it should be understood that various equivalents and modifications may exist at the time of filing this application.

Figure 1:
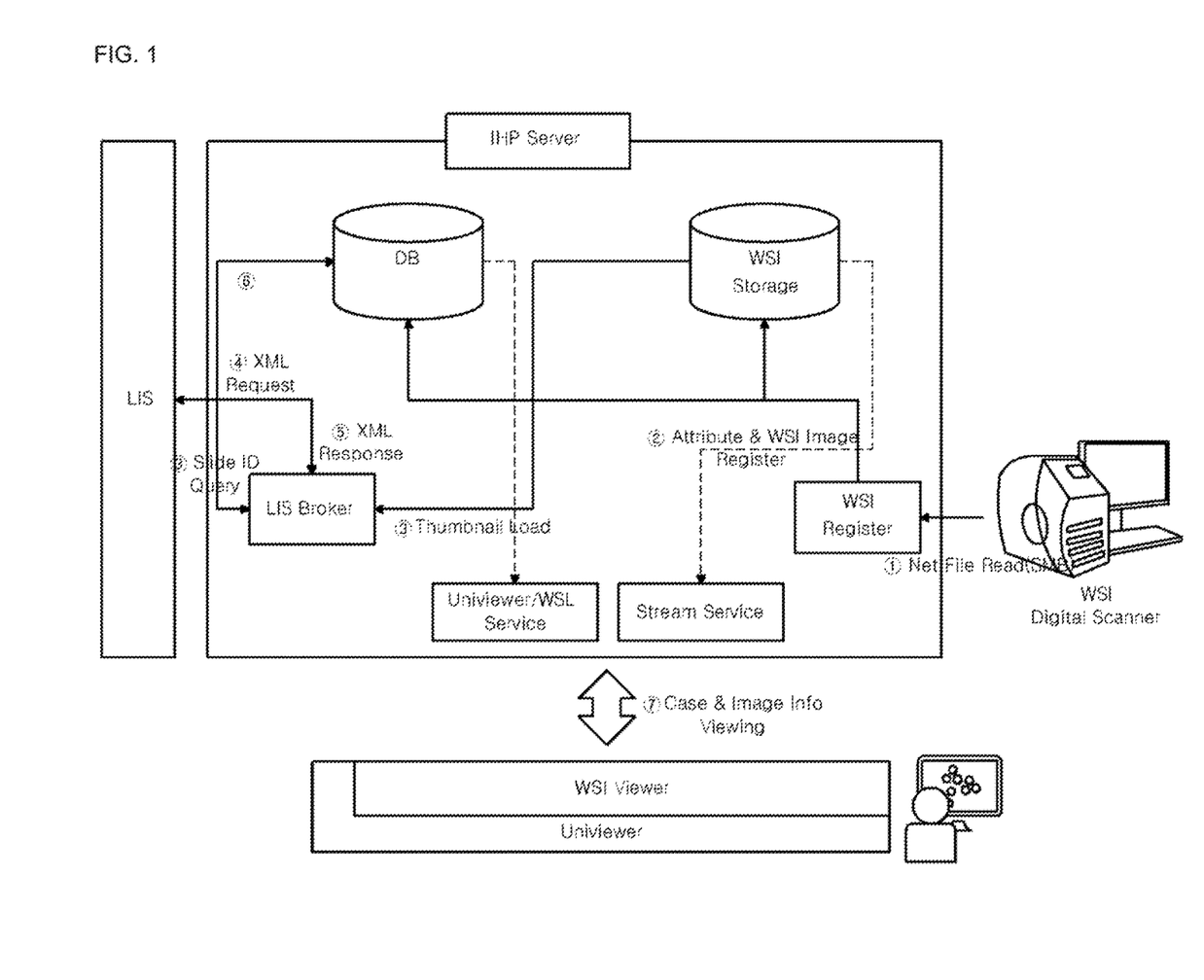
FIG. 1 is a schematic view of a system to which a patient case identity determination method for a digital pathology system according to the present invention is applied.
Figure 2:
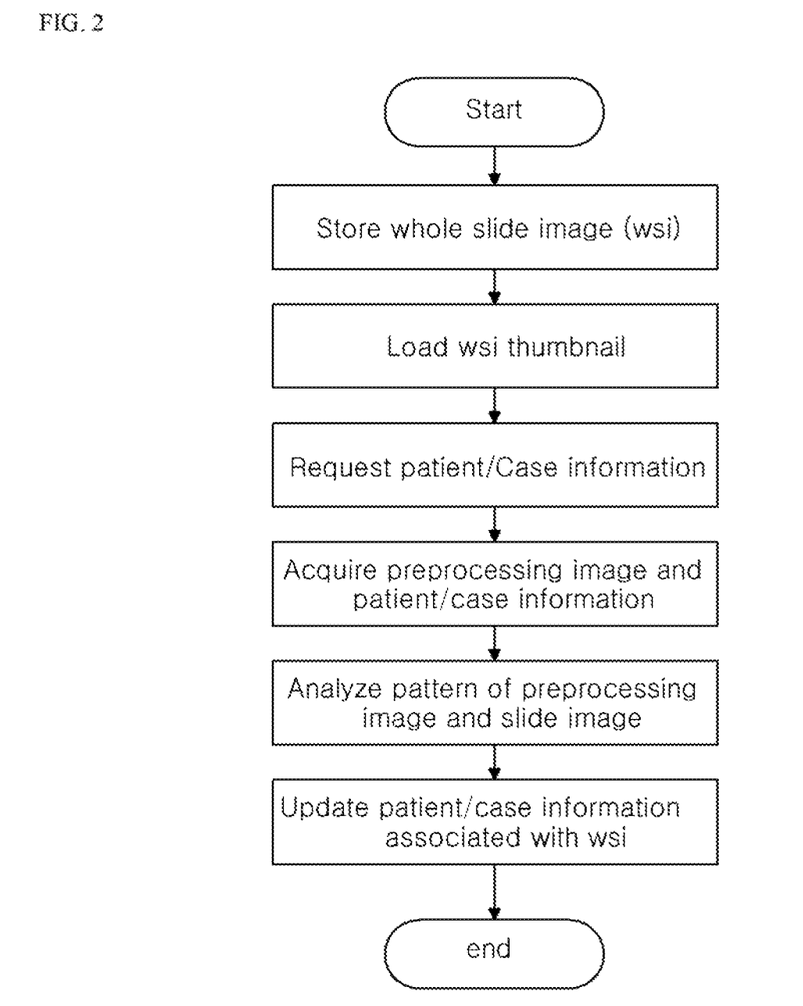
FIG. 2 is a flowchart of the patient case identity determination method for the digital pathology system according to the present invention.

FIG. 1 is a schematic view of a system to which a patient case identity determination method for a digital pathology system according to the present invention is applied, and FIG. 2 is a flowchart of the patient case identity determination method for the digital pathology system according to the present invention.

The digital pathology system to which the present invention is applied is applied to an image-based environment that is capable of acquiring, managing, and interpreting pathology information generated from digitized glass slides.

First, as shown in FIGS. 1 and 2, in the patient case identity determination method for the digital pathology system, a patient case identity determination unit acquires a digital slide image from a scanner (imaging modality).

Next, the patient case identity determination unit requests a laboratory information system (LIS) to send patient/case information including a preprocessing step image that is obtained in a digital slide preprocessing step associated with the digital slide image.

Next, the patient case identity determination unit receives the patient/case information including the preprocessing step image from the LIS.

Next, the patient case identity determination unit comparatively analyzes a pattern of the digital slide image and the preprocessing step image to calculate a synchronization rate and stores the calculated synchronization rate.

Next, when a client application provides a reading of the digital slide image, the patient case identity determination unit also provides information about whether the digital slide image is identical to the patient/case information based on the calculated synchronization rate. Thus, a user may check whether the current slide matches the patient/case information as soon as the user reads the digital slide image of the digital pathology system. In order to intuitively deliver information about whether the matching is achieved to the user, visual and/or auditory indications can be provided, especially, when the matching is not achieved.

Here, the client application may be a terminal configured to inquire about the digital slide image, analyze the digital sidle image, write an expert opinion (pathologist's opinion) on the digital slide image, or download the digital slide image.

In addition, the patient case identity determination unit may further perform a step of updating the patient/case information when the synchronization rate satisfies a certain criterion.

In order to calculate the synchronization rate, an example will be provided below.

Figure 3:
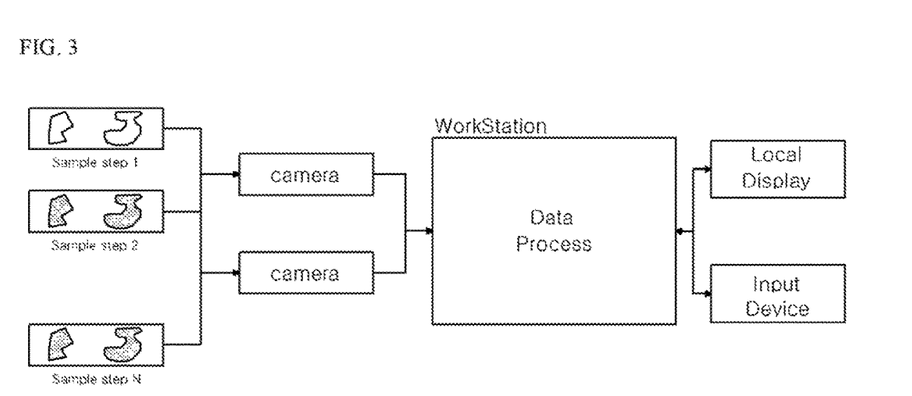
FIG. 3 is a view showing a system according to the present invention.
Figure 15:
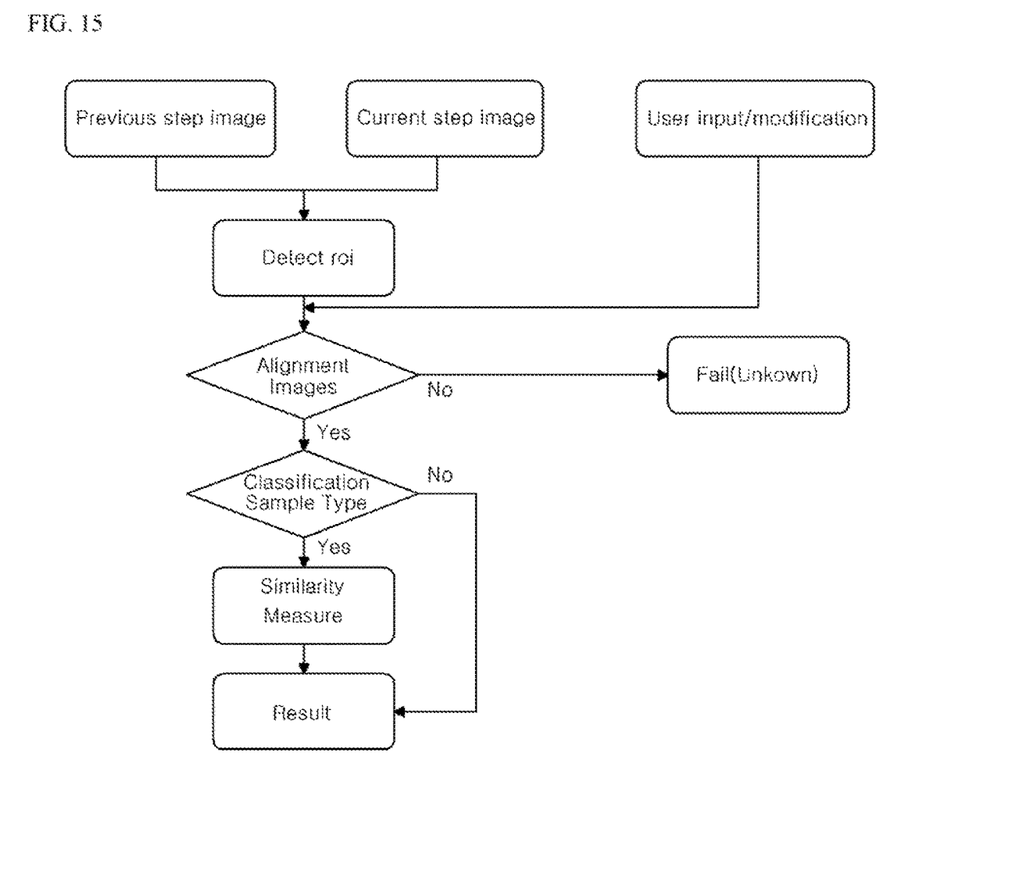
FIG. 15 is a flowchart showing a sample similarity measurement method for a digital pathology system according to the present invention.

FIG. 3 is a view showing a system according to the present invention, and FIG. 15 is a flowchart showing a sample similarity measurement method for a digital pathology system according to the present invention.

As shown in FIGS. 3 and 15, a sample similarity measurement method for determining a synchronization rate for a digital pathology system according to an embodiment of the present invention is a method of measuring sample similarity in a processing process of the digital pathology system. The sample similarity measurement method includes extracting a first main area and a second main area from each of a first digital slide image and a second digital slide image, aligning the first main area and the second main area, classifying sample types of the first main area and the second main area when the alignment is successful, and measuring similarity of the first main area and the second main area when the sample types are the same.

Figure 4:
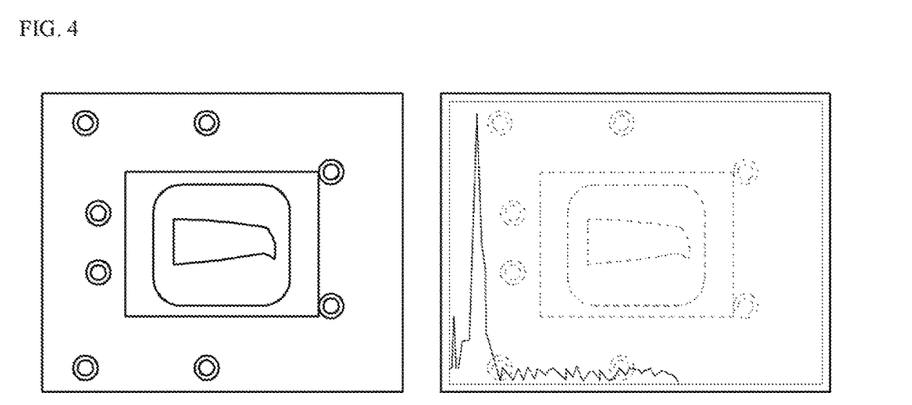
FIG. 4 is a view showing primary area classification that utilizes a color distribution chart for a digital slide image in order to extract a main area.
Figure 5:
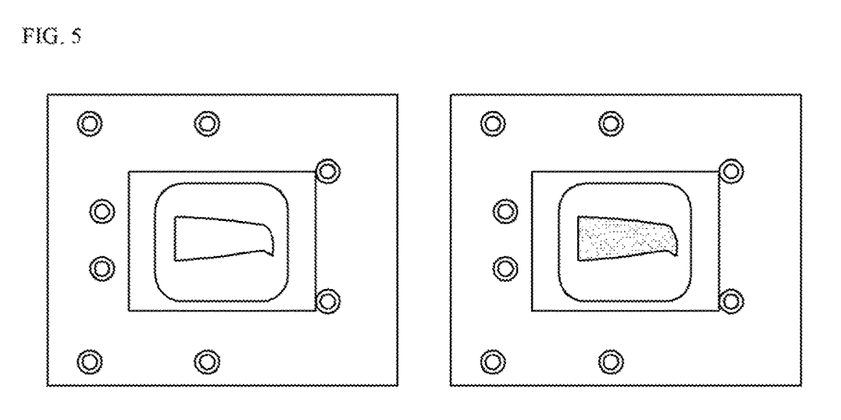
FIG. 5 is a view showing a step of detecting a main area through color bleaching after the primary area classification.
Figure 11:
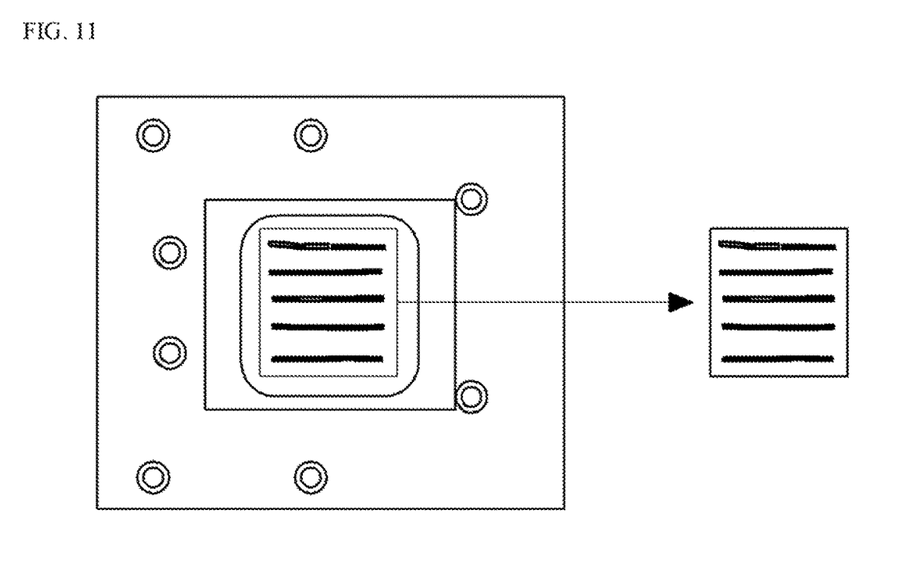
FIG. 11 is a view showing an example of extracting a main area in a digital pathology system according to the present invention.

FIG. 11 is a view showing an example of extracting a main area (ROI, region of interest) in a digital pathology system according to the present invention. In more detail, FIG. 4 is a view showing primary area classification that utilizes a color distribution chart (graph in right figure of FIG. 4) for a digital slide image in order to extract a main area, and FIG. 5 is a view showing a step of detecting a main area through color bleaching (decolorization) after the primary area classification. The left and right figure in FIG. 5 are the image before and after the decolorization. As shown in FIGS. 4 and 5, as the method of measuring sample similarity in a processing process for a digital pathology system, a method of detecting a main area through a color distribution chart in the image, that is, a method of automatically detecting a main area through separation of the color of the sample from background may be used.

Figure 12:
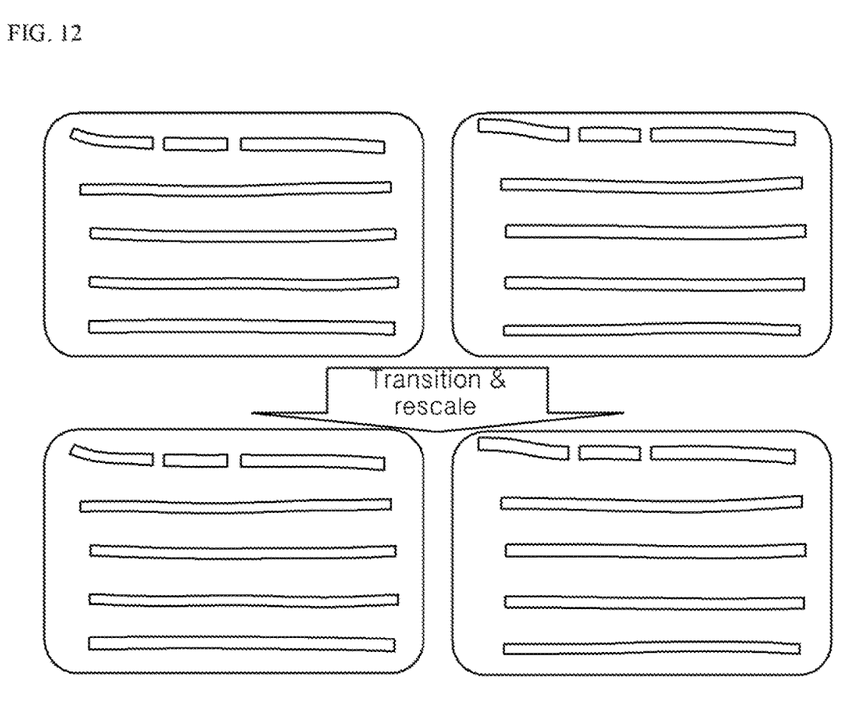
FIG. 12 is a view showing an example of aligning a first main area and a second main area extracted in a digital pathology system according to the present invention.

Next, as shown in FIG. 12, the extracted first main area (ROI) and second main area (ROI) are aligned. Here, the alignment conceptually includes rotation and rescaling in addition to up-down and left-right movement. A candidate for the up-down and left-right movement and a candidate for an angle for the rotation are determined, and whether the number of feature points before the movement and the number of feature points after the movement are the same or similar to each other is determined. Then, a final value for the up-down and left-right movement and a final value for the rotational angle may be determined. In this case, a step of determining that the sample similarity measurement has failed when the alignment fails may be further included.

Next, when the alignment is successful, sample types of the first main area and the second main area are classified. Here, the classifying of sample types includes determining whether there is a single sample or there are multiple samples through the number of central points detected in the first main area and the second main area; determining sizes of the samples of the first main area and the second main area; determining an arrangement shape of the samples as one of a vertical arrangement, a horizontal arrangement, and a mixture arrangement through an up-down and left-right position relation between the detected central points, and classifying types of the samples based on the singularity/ plurality determination of the samples, the sizes of the samples, and the arrangement shape of the samples.

Figure 6:
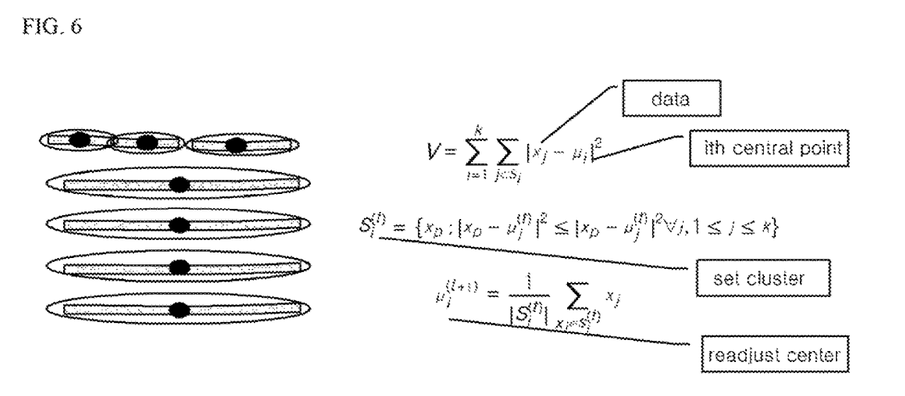
FIG. 6 is a view illustrating a method of detecting a center point of an object through K-means clustering.

In detail, as shown in FIG. 6, the central point of an object is detected through K-means clustering, and whether there is a single sample or there are multiple samples in a digital slide image is determined through the number of central points that are detected.

A K-means clustering algorithm divides a data set of image pixels as clusters having a similar property.

The first equation in FIG. 6 finds the entire variation between a point $x_\varphi$ of a jth cluster and a center $\mu_\tau$ of ith cluster. In the equation, $S_\tau$ denotes a set of points belonging to a cluster, and k denotes the number of clusters that are initialized. The first equation finds a set of points for minimizing the sum of the entire variance, which is an objective of the K-means algorithm.

The second equation in FIG. 6 resets data in a cluster. That is, a cluster to which data has to belong is reset by comparing a center $\mu_\tau$ of the current cluster and a center $\mu_\varphi$ of any other cluster. In the second equation, $S_\tau^{(t)}$ denotes a set of points belonging to an ith cluster, $x_\pi$ denotes the current comparison target, and j is a natural number that is less than or equal to k.

The last equation in FIG. 6 updates each cluster center $\mu_\tau$ as the center of the reset data cluster. In this equation, a variable $|S_j^{(t)}|$ is the number of points in $S_\tau^{(t)}$, and $x_\varphi$ denotes a point in $S_\tau^{(t)}$. That is, by dividing the sum of values of all points of $S_\tau^{(t)}$ by the number of points, a readjustment to $\mu_\tau^{(t+1)}$, which is a (t+1)th average, is performed. The K-means algorithm repeats the second equation and the last equation until the cluster is not changed.

The arrangement shape of the samples is determined as one of a vertical arrangement, a horizontal arrangement, and a mixture arrangement through an up-down and left-right position relation between the detected central points.

Figure 7:
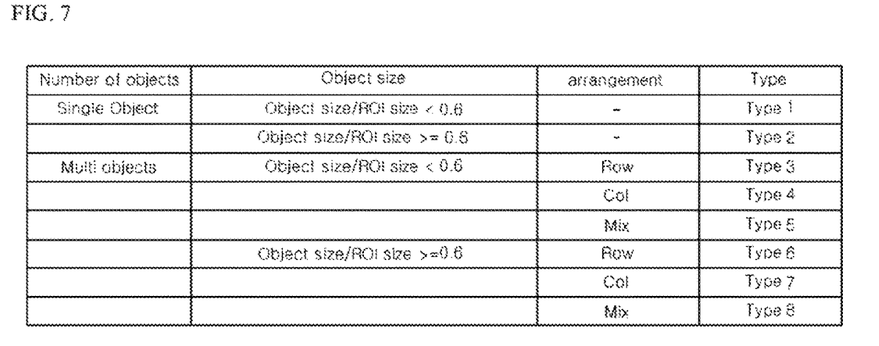
FIG. 7 is a table showing a criterion for classifying sample types.

FIG. 7 is a view showing a criterion for classifying sample types. For example, when there is one sample, and the size of the sample or the size of the main area is smaller than 0.6, the sample is classified as type 1. When there are multiple samples, the size of the samples or the size of the main area is greater than or equal to 0.6, and also the samples are arranged in a row, the samples are classified as type 6.

Figure 8:
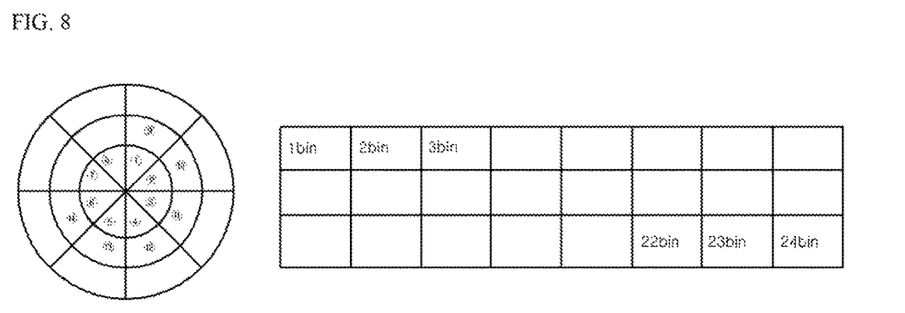
FIG. 8 is a view showing an example of performing a division into 24 sections to set a search section and storing information about each section in a comparison descriptor storage for an edge point.
Figure 9:
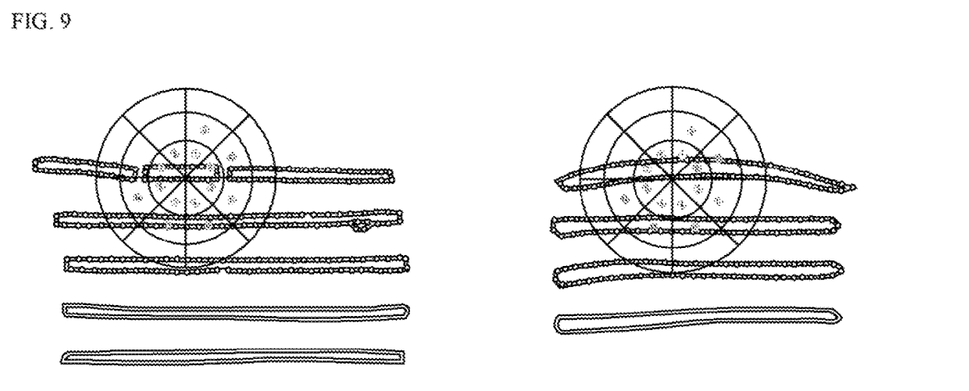
FIG. 9 is an exemplary view showing a comparison using information about 24 sections.

Next, the similarity of the first main area and the second main area is measured. In this case, when there is one sample, similarity is measured through shape information of the sample, color information of the sample, and edge directivity and intensity of the sample. The edge directivity and intensity of the sample are measured by performing cutting with three concentric circles and at an angle of 45 degrees with respect to edge points corresponding to the first main area and the second main area, performing a division into 24 sections to set a search section (each section includes the number of surrounding edge points in the section, average color information of the surrounding edge points in the section, average edge intensity of the surrounding edge points in the section, and vector direction information of the surrounding edge points in the section), comparing information about the 24 sections of the edge points corresponding to the first main area and the second main area. In this case, the similarity may also employ the number or rate of sections that are identical among 24 sections. In more detail, the number or rate of cases in which the number of surrounding edge points in the section, average color information of the surrounding edge points in the section, average edge intensity of the surrounding edge points in the section, or vector direction information of the surrounding edge points in the section is identical may also be employed as the similarity.

Figure 10:
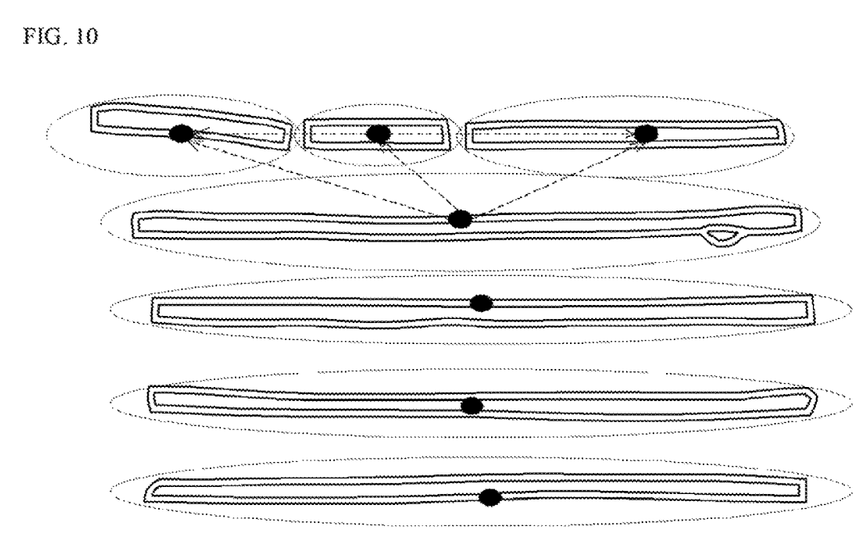
FIG. 10 is a view showing an example of measuring information about distances among centers of multiple samples.

In addition, when there are multiple samples, the similarity may be measured in the same way as that of the case in which there is a single sample. However, the similarity may be measured by adding information regarding distances between objects in the sample and a cluster shape in which the objects are formed, in addition to shape information of the sample, color information of the sample, and edge directivity and intensity of the sample.

In addition, a step of determining that the samples are different and ending the measurement when the sample types are classified as being different may be further included.

FIG. 8 is a view showing an example of performing a division into 24 sections to set a search section and storing information about each section in a comparison descriptor storage for an edge point, FIG. 9 is a view showing a comparison using information about the 24 sections, and FIG. 10 is a view showing an example of measuring information about distances among the centers of multiple samples.

Figure 13:
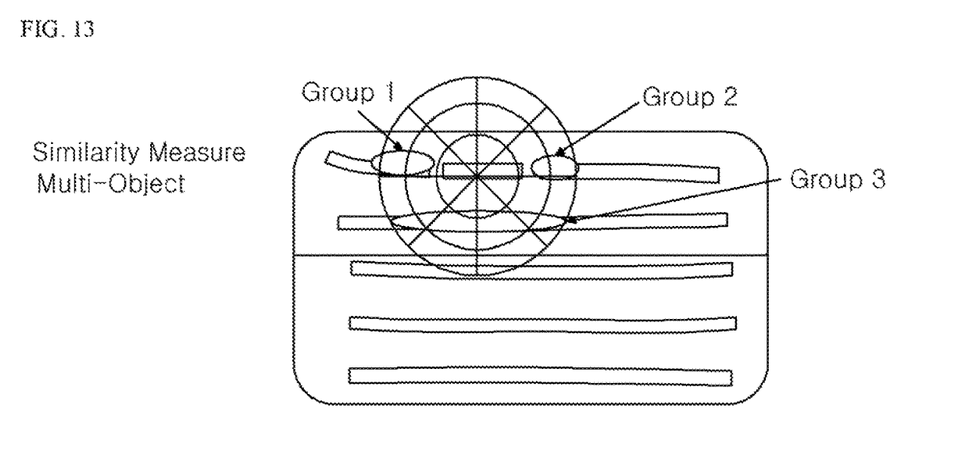
FIG. 13 is a view illustrating an example of measuring similarity of multiple samples.
Figure 14:
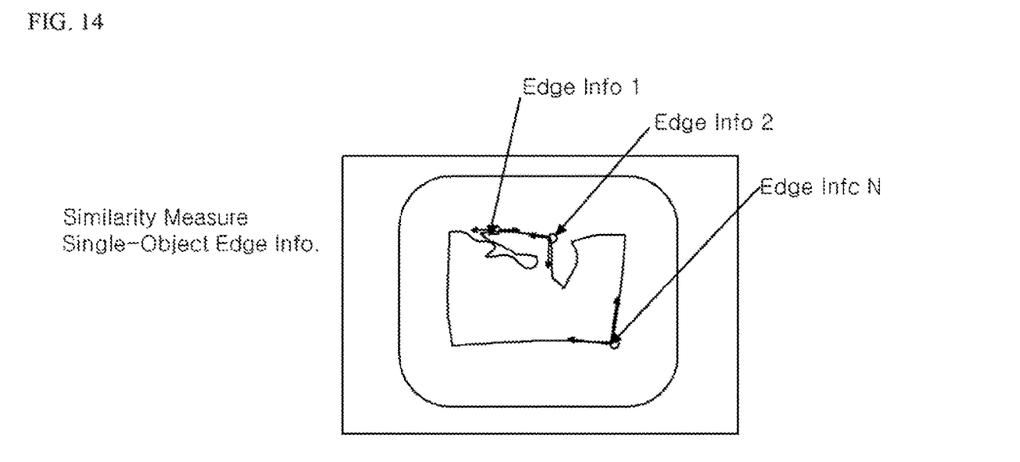
FIG. 14 is a view illustrating an example of similarity measurement using edge information for a single sample.

FIG. 13 is a view illustrating an example of measuring similarity of multiple samples, and FIG. 14 is a view illustrating an example of measuring similarity using edge information for a single sample.

The patient case identity determination method for the digital pathology system according to the present invention may solve a problem in which human errors are likely to occur when a task of adding a manual barcode is performed in each of the preprocessing steps of producing a digital slide image, i.e., grossing, waxing, paraffin blocking, sectioning, or staining.

That is, because there is no fundamental way to block human errors, the human errors are prevented by analyzing an image pattern of an image that is captured in a preprocessing step of the digital pathology system and an image pattern of a digital slide image that is a final result, determining, at the acquisition time of the digital slide image, whether there is a match, and then informing a user of a result of the determination.

While the present invention has been described with reference to a few specific embodiments, the description is illustrative of the invention and is not to be construed as limiting the invention. Various modifications may occur to those skilled in the art without departing from the spirit and scope of the invention as defined by the appended claims and their equivalents.

What is claimed is:

1. A method of determining a patient case identity using a digital pathology system, which is performed by a patient case identity determination unit, the method comprising:
    acquiring a first digital slide image from a scanner;
    requesting a laboratory information system (LIS) to send patient/case information including a second digital slide image that is obtained in a digital slide preprocessing associated with the first digital slide image;
    receiving the patient/case information including the second digital slide image from the LIS;
    comparatively analyzing a pattern of the first digital slide image and a pattern of the second digital slide image to calculate a synchronization rate and storing the calculated synchronization rate; and
    providing information about whether the first digital slide image is identical to the second digital slide image of the patient/case information based on the calculated synchronization rate when a client application provides a reading of the first digital slide image,
    wherein the comparatively analyzing the pattern of the first digital slide image and the pattern of the second digital slide image comprises:
        extracting a first main area of the first digital slide image and a second main area of the second digital slide image;
        aligning the first main area and the second main area;
        classifying sample types of the first main area and the second main area when the alignment is successful; and
        measuring similarity of the first main area and the second main area when the sample types are the same.

2. The method of claim 1, wherein the client application is a terminal configured to inquire about the first digital slide image, analyze the first digital slide image, write an expert opinion on the first digital slide image, or download the first digital slide image.

3. The method of claim 2, further comprising updating the patient/case information when the synchronization rate satisfies a certain criterion.

4. The method of claim 3, wherein, in the step of providing the information about whether the first digital slide image is identical to the second digital slide image of the patient/case information,
    when it is determined that the first digital slide image is not identical to the second digital slide image of the patient/case information based on the synchronization rate, the patient case identity determination unit provides visual and/or auditory indications in order to intuitively deliver a non-identity to the user.

5. The method of claim 1, wherein the classifying of the sample types comprises:
    determining whether there is a single sample or there are a plurality of samples through a number of central points detected in the first main area and the second main area;
    determining sizes of the samples of the first main area and the second main area;
    determining an arrangement shape of the samples as one of a vertical arrangement, a horizontal arrangement, and a mixture arrangement through an up-down and left-right position relation between the detected central points; and
    classifying types of the samples based on the singularity/plurality determination for the samples, the sizes of the samples, and the arrangement shape of the samples.

6. The method of claim 5, wherein, in the step of measuring of the similarity of the first main area and the second main area,
    when there is the single sample, measuring the similarity through shape information of the sample, color information of the sample, and edge directivity and intensity of the sample,
    wherein the edge directivity and the intensity of the sample are measured by:
        performing cutting with three concentric circles and at an angle of 45 degrees with respect to edge points corresponding to the first main area and the second main area,
        performing a division into 24 sections to set a search section, each section including a number of surrounding edge points in the section, average color information of the surrounding edge points in the section, average edge intensity of the surrounding edge points in the section, and vector direction information of the surrounding edge points in the section, and comparing information about the 24 sections of the edge points corresponding to the first main area and the second main area.

7. The method of claim 5, wherein, in the step of measuring of similarity of the first main area and the second main area, when there is the plurality of samples, measuring the similarity through shape information of the sample, color information of the sample, and edge directivity and intensity of the sample, information regarding distances between objects in the sample, and a cluster shape in which the objects are formed.

8. The method of claim 7, further comprising determining whether the similarity measurement has failed when the alignment fails.

9. The method of claim 7, further comprising determining whether the samples are different and ending the measurement when the sample types are classified as being different.

* * * * *